(12) United States Patent
Brassell et al.

(10) Patent No.: US 6,948,391 B2
(45) Date of Patent: Sep. 27, 2005

(54) PROBE WITH INTEGRAL VENT, SAMPLING PORT AND FILTER ELEMENT

(75) Inventors: Gilbert Brassell, Golden, CO (US); Terry J. Wickland, Evergreen, CO (US); Darold M. Popish, Golden, CO (US)

(73) Assignee: Nuclear Filter Technology, Golden, CO (US)

( * ) Notice: Subject to any disclaimer, the term of this patent is extended or adjusted under 35 U.S.C. 154(b) by 208 days.

(21) Appl. No.: 10/393,290

(22) Filed: Mar. 21, 2003

(65) Prior Publication Data

US 2004/0182181 A1 Sep. 23, 2004

(51) Int. Cl.[7] .............................................. G01N 1/14
(52) U.S. Cl. ................................. 73/863.84; 73/864.74
(58) Field of Search ......................... 73/863.23, 863.33, 73/863.83, 863.84, 863.85, 864.34, 864.74; 137/318, 319; 220/367.1, 371, 372

(56) References Cited

U.S. PATENT DOCUMENTS

| 4,231,488 | A | | 11/1980 | Ward et al. |
| 4,500,328 | A | | 2/1985 | Brassell et al. |
| 4,756,852 | A | | 7/1988 | Temus |
| 4,957,518 | A | | 9/1990 | Brassell |
| 4,957,522 | A | | 9/1990 | Brassell |
| 5,131,283 | A | * | 7/1992 | Canfield ................... 73/864.74 |
| 5,193,709 | A | * | 3/1993 | Brassell ....................... 220/371 |
| 5,353,949 | A | | 10/1994 | Seibert et al. |
| 5,634,484 | A | | 6/1997 | Vodila et al. |
| 5,720,789 | A | | 2/1998 | Pinson |
| 5,725,645 | A | | 3/1998 | Wickland et al. |
| 5,727,707 | A | | 3/1998 | Wickland et al. |
| 5,767,422 | A | | 6/1998 | Brassell et al. |
| 5,891,223 | A | * | 4/1999 | Shaw et al. .................... 96/134 |
| 5,911,332 | A | | 6/1999 | Wickland et al. |
| 6,041,669 | A | * | 3/2000 | Brassell et al. ........... 73/864.74 |
| 6,076,410 | A | * | 6/2000 | Renslow ................... 73/864.34 |
| 6,089,399 | A | | 7/2000 | Felbaum et al. |
| 6,095,356 | A | | 8/2000 | Rits |
| 6,293,163 | B1 | * | 9/2001 | Johnston et al. ........... 73/864.7 |
| 6,395,050 | B1 | | 5/2002 | Wickland et al. |
| 6,413,304 | B1 | | 7/2002 | Wickland et al. |

* cited by examiner

Primary Examiner—Robert Raevis
(74) Attorney, Agent, or Firm—Millen, White, Zelano & Branigan, P.C.

(57) ABSTRACT

A probe with an integral filtered vent and sampling port has a hollow shaft configured as a drill bit which in use passes through the lid of a drum containing waste products within a liner. The hollow shaft has a penetrating tip and at lest two radial bores, one of which is positioned to open to the space within the liner and the other of which is positioned to open to the space above the liner and between the liner and drum lid. The shaft has a head with a pocket which contains a filter element, the head also having a radial sampling port with a septa seal. In order to sample head space gases, a hypodermic needle is pushed through the septa seal into the longitudinal bore of the hollow shaft, and then withdrawn, allowing the septa seal to close behind the needle. The probe is especially useful for sampling nuclear waste stored within drums having liners. This is because the probe has a first radial port adjacent the penetrating tip thereof which samples gas within the liner and a second radial port disposed between the liner and lid for sampling gas which has escaped past the liner.

23 Claims, 3 Drawing Sheets

PROBE WITH INTEGRAL VENT, SAMPLING PORT AND FILTER ELEMENT

FIELD OF THE INVENTION

The present invention is directed to a probe with an integral vent, sampling port and filter element, more particularly, the present invention is directed to a probe which is used to sample drums containing hazardous materials that emit gases.

BACKGROUND OF THE INVENTION

Nuclear waste is frequently packaged in drums which have lids that must be breached in order to test and vent head space gases. In the nuclear waste disposal industry, storage drums are used which have air spaces between the lid and waste that over time can accumulate hazardous gases. In order to legally ship these drums safely, these gases must be sampled and vented. Currently, drum lids are vented by using a bung vent filter or other screwed in venting filter. If the drum is already vented, and only needs to be sampled for gases, the drum vent must be removed or punctured in order to obtain the gas sample. Alternatively, a drum vent system such as that disclosed in U.S. Pat. No. 6,041,669 is used, and then another vent is installed through the lid of the drum while the sample is being obtained. If the drum has a liner, it is also necessary to puncture the liner in order to obtain a sample of any gases trapped between the liner and the stored nuclear waste. If for some reason the drum head space has to be sampled again, the entire procedure must be repeated and another hole put into the drum lid, or another filter replaced. Thus, the current procedures for venting and sampling drums are time consuming and somewhat complex.

SUMMARY OF THE INVENTION

In view of the aforedescribed considerations and other considerations, the present invention is directed to a probe with an integral vent, sampling port and filter element, wherein the probe comprises a hollow shaft with an axial bore therethrough having a penetrating tip at one end and a radial head at the other end. At least one first radial port extends through the hollow shaft and is in communication with the axial bore in proximity with the penetrating tip, and at least one second radial port extends though the hollow shaft; is in communication with the axial bore, and is in proximity with the radially extending head. A pocket is disposed in the radially extending head, the pocket being in communication with the axial bore. Within the pocket, a filter medium is disposed, and below the pocket a radial sampling port extending through the head is in communication with the axial bore. The radial sampling bore has a septa seal therein for receiving therethrough a shank of a sampling needle, the septa seal being disposed behind a removable plug.

In a further aspect of the invention, the probe is configured as a drill bit and has helical thread disposed adjacent to the radially extending head. A non-threaded portion extends from the helical thread to the penetrating tip.

In other aspects of the invention, at least one first radial port communicates with the longitudinal bore through the helical thread and the at least one second radial port communicates with the longitudinal bore through the unthreaded portion of the hollow shaft.

In still another aspect of the invention, the probe is made of stainless steel.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
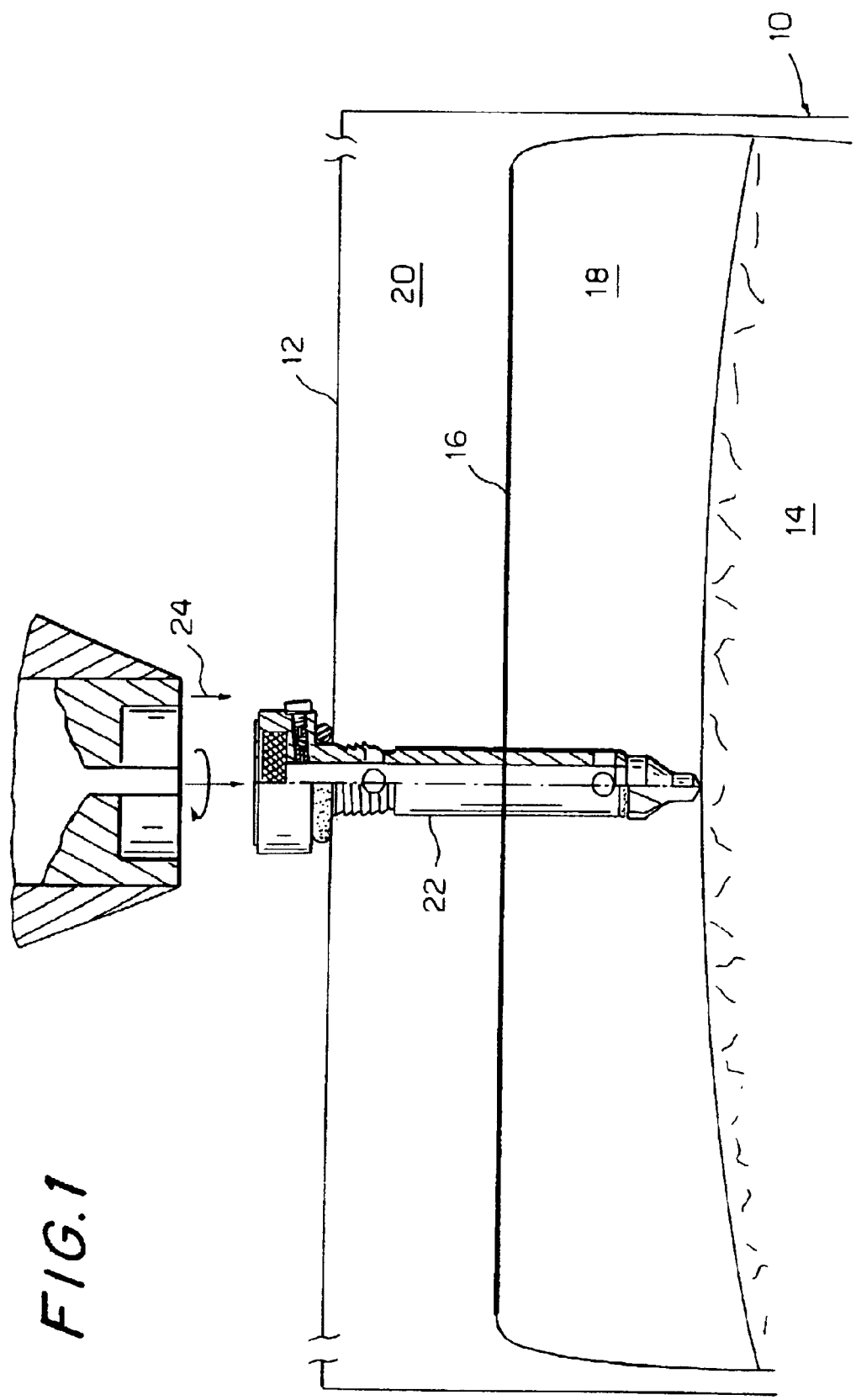
FIG. 1 is a side elevation showing the probe of the present invention penetrating both a lid and liner of a drum containing waste materials.

Referring now to FIG. 1, there is shown a cross section through a drum 10 covered by a lid 12 and containing solid nuclear waste 14 within a plastic vinyl liner 16. In order to vent and sample head space gases which may have accumulated both within a liner head space 18 and within a head space 20 between the lid 10 and liner 16, a probe 22 is inserted through both the lid 10 and liner 16. If the drum 10 does not have a liner 16, the probe will still work to filter, vent and allow sampling of head space gases between the solid waste 14 and lid. Preferably, the probe 22 is inserted by a drill bit 24 which grips and rotates the probe to drive the probe through the lid 12 and liner 16 when axial pressure is applied by the drill bit to the probe.

Figure 2:
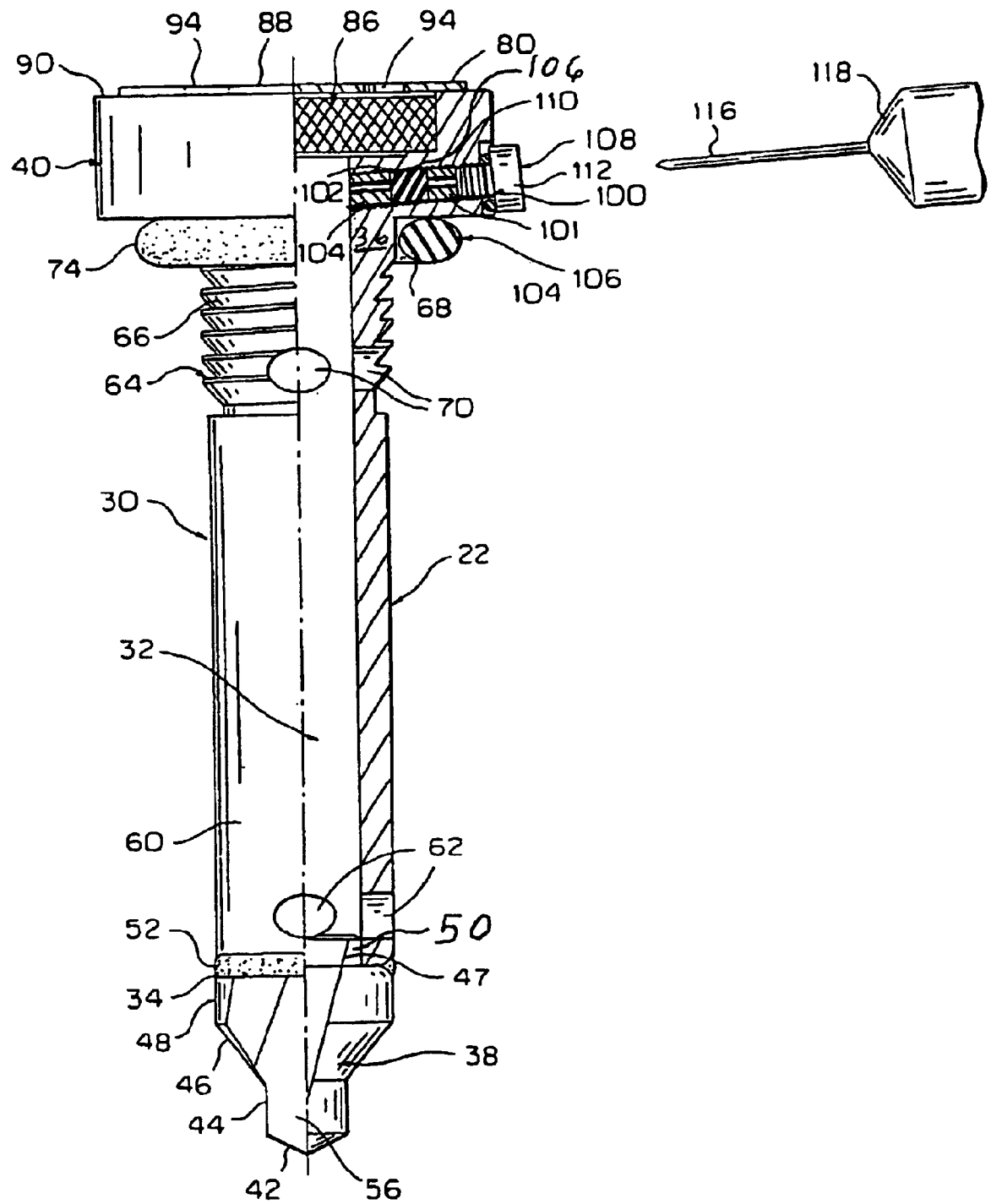
FIG. 2 is an enlarged view of the probe of FIG. 1.
Figure 3:
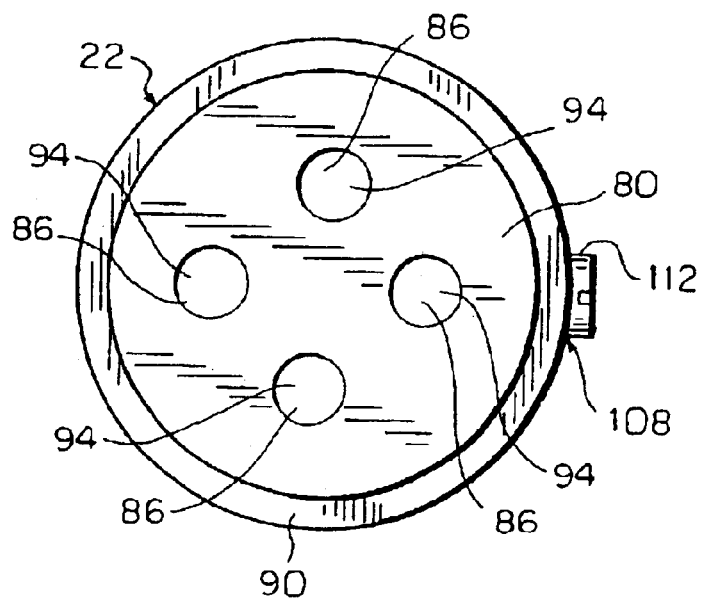
FIG. 3 is a top view of the probe of FIG. 1.
Figure 4:
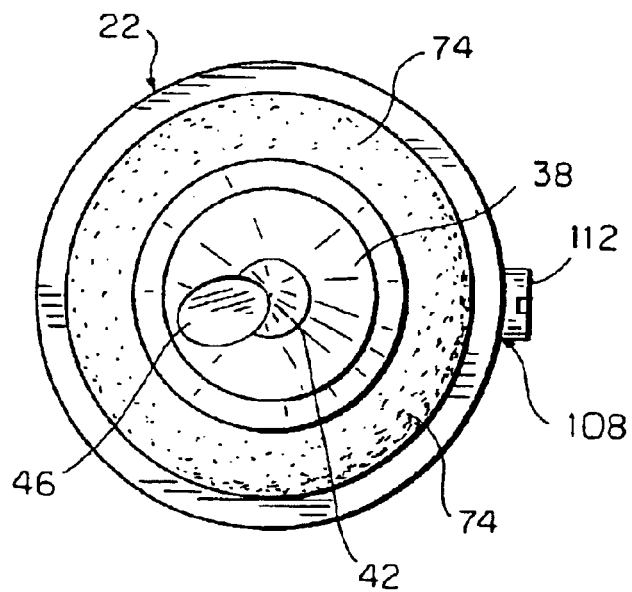
FIG. 4 is a bottom view of the drill bit of FIG. 1.

Referring now to FIG. 2 where the probe 22 is shown in greater detail, it is seen that the probe 22 has a hollow shaft 30 having a longitudinal bore 32, the hollow shaft having a first end 34 and a second end 36. A penetrating tip 38 is positioned at the first end 34 of the hollow shaft 30 and a radially extending probe head 40 is positioned at the second end 36 of the hollow shaft.

The penetrating tip 38 is a single piece having a conical portion 42 which is connected by a first cylindrical portion 44 to a frustoconical portion 46 that is in turn connected to a second cylindrical portion 48. The second cylindrical portion has a stud 50 of a smaller diameter than the cylindrical portion 48 projecting axially therefrom. The stud 50 is received within the longitudinal bore 32 of the hollow shaft 30 with a peripheral weld 52 securing the penetrating tip 38 to the hollow shaft.

An obtuse, longitudinally extending port 56 extends through the penetrating tip 38 from the conical portion 42. The longitudinally extending port 56 provides a channel for head space gases and gases within the hazardous waste 14 to flow into the longitudinal bore 32 (see FIG. 1).

Just above the penetrating tip 38 of the probe 22 extends a smooth punch portion 60 of the hollow shaft 30. Proximate to the stud 50 of penetrating tip 38, the smooth punch portion 60 has at least one, preferably four, first radial input ports 62 which pass through the wall of the hollow shaft 30 and communicate with the longitudinal bore 32. The smooth punch portion 60 has a smooth exterior surface so that it will slide through the vinyl liner 16 within the drum 10 after being inserted through the lid 12. As is seen in FIG. 1, the probe 22 is preferably inserted by drilling so that it rotates to cut its way through the drum lid 12 and then slides while rotating through the liner 16 without having the liner gripped and pulled upward by threads on the hollow shaft 30.

The unthreaded punch portion 60 of the hollow shaft 30 terminates at a location which is preferably adjacent the head 40. Above the punch portion 60 a threaded portion 64 begins with a helical thread 66. The helical thread 66 stops just before the radial head 40 of the hollow shaft 30 where the hollow shaft continues with a short smooth cylindrical portion 68. The helical thread 66 of the threaded portion 64 self-taps into the metal lid 12 as the probe 22 is rotated clockwise when driven by the rotating chuck 24 (see FIG. 1).

At least one radially opening second port 70 extends through the wall of the hollow shaft 30 to communicate with the head space 20 between the vinyl liner 16 and the lid 12. Consequently head space gas, which may escape from the vinyl liner into the head space 20 upon puncturing the liner with the probe 22, is also allowed to vent and can be sampled. While two radially opening second ports 70 are illustrated, there may be more. In the illustrated embodiment, the radial ports 70 are through the threaded portion 64 of the hollow shaft 30.

The smooth cylindrical portion 68 above the threaded portion 64 is surrounded by a gasket 74. The gasket 74 is preferably made of neoprene so as to have an extended life. The gasket 74 seals between the top surface of the lid 12 and the bottom surface of the radially extending head 40 (see FIG. 1).

The radially extending head 40 has a pocket 80 therein which receives a filter media 86, which may be, for example but not limited to, carbon-to-carbon, sintered stainless steel, ceramic, polyfiber material(s) or HEPA filter media, these filter media materials being employed either singularly or in combination. The filter media 86 filters elements down to 0.3 microns and is secured behind a vent cap 88 that is welded to the top surface 90 of the head 40. The vent cap 88 has holes 94 therethrough which allow filtered gas which has been vented from the drum 10 to vent to the atmosphere. While four holes 94 are illustrated, the number of holes may be more than or less than four.

On occasion, it is desirable to test the gases which are venting through the probe 22 from the interior of the container 10. This is accomplished by a radial vent port 100 that extends through the radially extending head 40 at a location beneath the filter media 86. The radial vent port 100 has threaded bore 101 which has therein a first septa retainer 102 and a second septa retainer 104. Between the retainers 102 and 104 is disposed a septa seal 106. A threaded plug 108, with a threaded shank 110 and head 112, which is slotted to receive a screwdriver, is threaded into the threaded bore 101 of the radial vent port 100 to close the vent port when not in use.

Samples are taken through the vent port 100 by a needle 116 of a syringe 118. The needle 116 passes through bores in the septa retainers 102 and 104 and through the resilient, elastic material of the septa seal 106 to take a sample from the longitudinal bore 32 of the hollow shaft 30. Upon withdrawing the needle 116, the septa seal 106 closes so that whatever gaseous products remaining in the longitudinal bore 32 must pass through the filter element 86 before venting to the atmosphere.

While the probe 22 is especially useful for drums 10 containing nuclear waste products, it can be also useful for sampling the contents of drums containing other waste products, or any other solid or semi-solid material which needs to be vented and sampled.

From the foregoing description, one skilled in the art can easily ascertain the essential characteristics of this invention, and without departing form the spirit and scope thereof, can make various changes and modifications of the invention to adapt it to various usages and conditions.

We claim:

1. A probe with an integral vent and sampling port, comprising:
    a hollow shaft with an axial bore therethrough, the shaft having a penetrating tip at a first end and a radially extending head at a second end;
    at least one first radial port extending through the hollow shaft and in communication with the axial bore in proximity with the penetrating tip;
    at least one second radial port extending through the hollow shaft and in communication with the axial bore in proximity with the radial extending head, a pocket being in communication with the axial bore,
    a filter medium disposed in the pocket, and
    a radial sampling port in the head communicating at a first end and with the axial bore, the radial sampling bore having a septa seal therein for receiving therethrough a shank of a sampling needle and a removable plug at a second end.

2. The probe of claim 1 wherein the shaft has a helical thread disposed thereon at least adjacent to the radially extending head.

3. The probe of claim 2 wherein the probe is made of stainless steel.

4. The probe of claim 3 wherein a gasket is disposed around the hollow shaft in abutment with the radially extending head.

5. The probe of claim 4 further including an axially extending port through the penetrating tip into the axial bore through the hollow shaft.

6. The probe of claim 5 wherein the axially extending port is at an angle which is obtuse to the axially extending bore.

7. The probe of claim 1 wherein the probe is made of stainless steel.

8. The probe of claim 1 wherein the probe is made of stainless steel.

9. The probe of claim 1 wherein the probe is configured as a drill bit with an unthreaded punch portion extending from the penetrating tip toward the head and has a helically threaded portion extending from the head toward the tip, the unthreaded and threaded portions meeting intermediate the ends of the hollow shaft.

10. The probe of claim 9 wherein the second port is disposed within the threaded portion of the hollow shaft.

11. The probe of claim 1 wherein the penetrating tip has at least one tapered portion for initially penetrating a wall of a container, the tapered portion having an axially extending port therethrough in communication with the longitudinal bore.

12. The probe of claim 11 wherein the axially extending port extends through a tapered portion of the penetrating tip.

13. A probe with an integral vent and sampling port for testing material within a drum liner which itself is enclosed by a drum having a wall portion, comprising:
    a hollow shaft with an axial bore therethrough, the shaft having a penetrating tip at a first end for penetrating at least the wall portion of the drum and a radially extending head at a second end for engaging the outer surface of the wall portion;
    at least one first radial port extending through the hollow shaft and in communication with the axial bore in proximity with the penetrating tip;
    at least one second radial port extending through the hollow shaft and in communication with the axial bore in proximity with the radial extending head, a pocket being in communication with the axial bore, a filter medium disposed in the pocket, and a radial sampling port in the head communicating at a first end and with the axial bore, the radial sampling bore having a septa seal therein for receiving therethrough a shank of a sampling needle and a removable plug at a second end.

14. The probe of claim 13 wherein the shaft has a helical thread disposed thereon at least adjacent to the radially extending head for threadably engaging the wall portion.

15. The probe of claim 14 wherein the probe is made of stainless steel.

16. The probe of claim 15 wherein a gasket is disposed around the hollow shaft in abutment with the radially extending head for engaging the outside surface of the wall.

17. The probe of claim 13 wherein the probe is configured as a drill bit with an unthreaded punch portion extending from the penetrating tip toward the head and wherein the probe has a helically threaded portion extending from the head toward the tip, the unthreaded and threaded portions meeting intermediate the ends of the hollow shaft, wherein the unthreaded portion passes through the liner to sample fluids within the liner with the first port and the second port remains in a space between the liner and wall portion of the drum to sample fluids within the space.

18. The probe of claim 17 wherein the probe is made of stainless steel.

19. The probe of claim 17 wherein the penetrating tip has at least one tapered portion for initially penetrating the wall portion of the drum, the tapered portion having an axially extending port therethrough in communication with the longitudinal bore.

20. The probe of claim 19 wherein the axially extending port extends through a tapered portion of the penetrating tip.

21. The probe of claim 13 wherein the wall portion is a lid on the drum, the lid being displaced from the liner to define a space between the lid and liner, the space being accessed by the second radial port when the first radial port is within the liner to sample fluid within the liner.

22. The probe of claim 21 wherein the probe is stainless steel and the material is nuclear waste.

23. The probe of claim 1 in combination with a container for containing transuranic waste, the probe being constructed and arranged for penetrating a lid of the container to sample gas eminating from the waste.

* * * * *

UNITED STATES PATENT AND TRADEMARK OFFICE
CERTIFICATE OF CORRECTION

PATENT NO. : 6,948,391 B2 Page 1 of 1
DATED : September 27, 2005
INVENTOR(S) : Gilbert Brassell et al.

It is certified that error appears in the above-identified patent and that said Letters Patent is hereby corrected as shown below:

<u>Column 4,</u>
Line 34, reads "probe of claim 1 wherein the probe is" should read -- probe of claim 5 wherein the probe --.

Signed and Sealed this

Thirteenth Day of June, 2006

JON W. DUDAS
*Director of the United States Patent and Trademark Office*